United States Patent
Fleischman et al.

(10) Patent No.: US 6,241,724 B1
(45) Date of Patent: Jun. 5, 2001

(54) SYSTEMS AND METHODS FOR CREATING LESIONS IN BODY TISSUE USING SEGMENTED ELECTRODE ASSEMBLIES

(75) Inventors: Sidney D. Fleischman, Sunnyvale; David K. Swanson, Mountain View; Russell A. Houser, Livermore; Omar M. Amirana, Sunnyvale, all of CA (US)

(73) Assignee: EP Technologies, Inc., Sunnyvale, CA (US)

( * ) Notice: Subject to any disclaimer, the term of this patent is extended or adjusted under 35 U.S.C. 154(b) by 0 days.

(21) Appl. No.: 08/604,192

(22) Filed: Feb. 21, 1996

Related U.S. Application Data

(63) Continuation of application No. 08/139,304, filed on Oct. 19, 1993, now abandoned.

(51) Int. Cl.[7] ............................................. A61B 18/14
(52) U.S. Cl. ..................... 606/41; 606/34; 600/374; 607/99; 607/122
(58) Field of Search ............................. 606/41, 49, 34; 607/99, 113, 116, 119, 122; 600/374

(56) References Cited

U.S. PATENT DOCUMENTS

| | | | |
|---|---|---|---|
| 4,224,949 | * 9/1980 | Scott et al. | 128/642 |
| 4,365,639 | 12/1982 | Goldreyer. | |
| 4,785,815 | * 11/1988 | Cohen | 128/642 |
| 4,848,352 | * 7/1989 | Pohndorf et al. | 607/122 |
| 4,940,064 | 7/1990 | Desai. | |
| 4,955,382 | * 9/1990 | Franz et al. | 128/642 |
| 5,156,151 | * 10/1992 | Imran | 128/642 |
| 5,275,162 | * 1/1994 | Edwards et al. | 128/642 |
| 5,281,213 | * 1/1994 | Milder et al. | 607/122 |
| 5,314,466 | * 5/1994 | Stern et al. | 606/41 |
| 5,341,807 | * 8/1994 | Nardella | 606/41 |
| 5,454,809 | * 10/1995 | Janssen | 606/41 |
| 5,718,701 | * 2/1998 | Shai et al. | 607/99 |

FOREIGN PATENT DOCUMENTS

| | | | |
|---|---|---|---|
| 5-23399 | 2/1993 | (JP). | |
| 93/08757 | * 5/1993 | (WO) | 606/41 |

* cited by examiner

*Primary Examiner*—Lee Cohen
(74) *Attorney, Agent, or Firm*—Lyon & Lyon LLP

(57) ABSTRACT

A multiple electrode array for ablating tissue carries at least two electrode segments that are circumferentially spaced from each other. Insulation electrically isolates the separated electrode segments from each other. Signal wires attached to the separated electrode segments convey ablating energy independently to the separated electrode segments. Because of its segmented structure, the array can place only one of the electrode segments in contact with tissue at one time. Because each segment is electrically isolated, and because each segment is independently served by its own signal wire, a physician can operate an ablation energy generator to selectively channel the ablation energy only to the segment actually contacting the tissue.

13 Claims, 8 Drawing Sheets

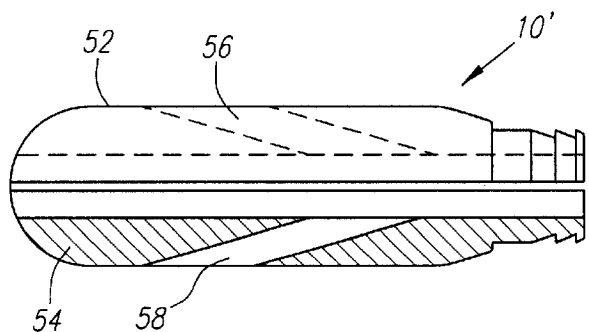
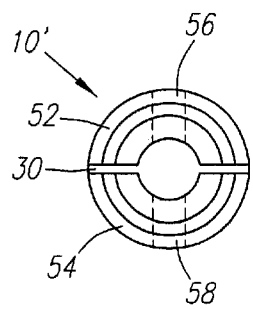
FIG. 8           FIG. 9
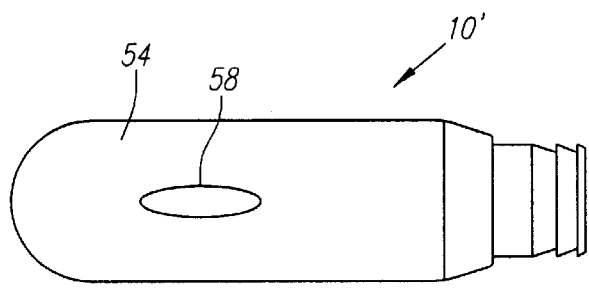
FIG. 10
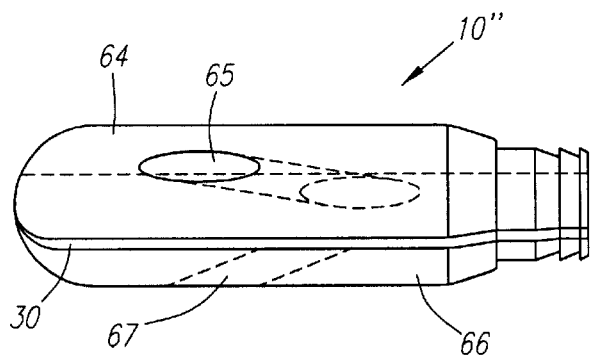
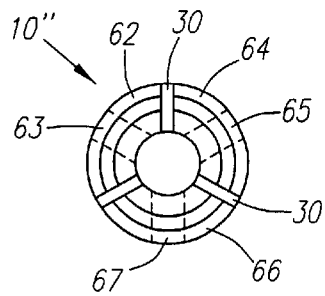
FIG. 11          FIG. 12

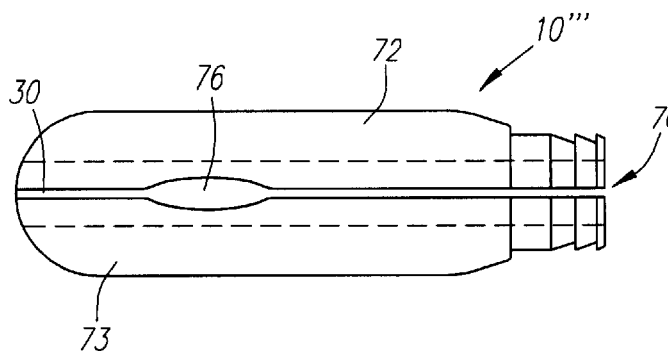
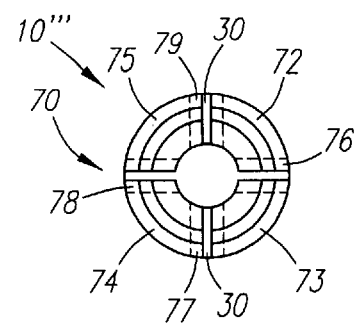
FIG. 13    FIG. 14
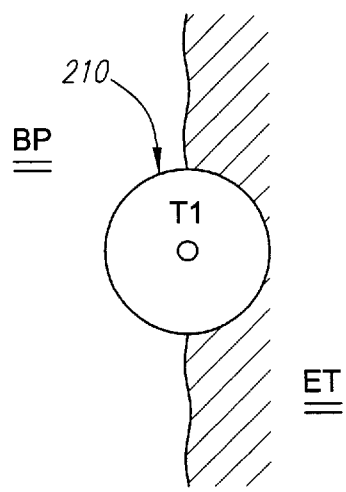
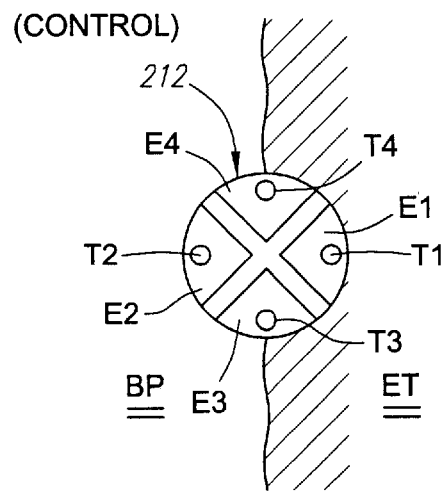
FIG. 15    FIG. 16
(PRIOR ART)
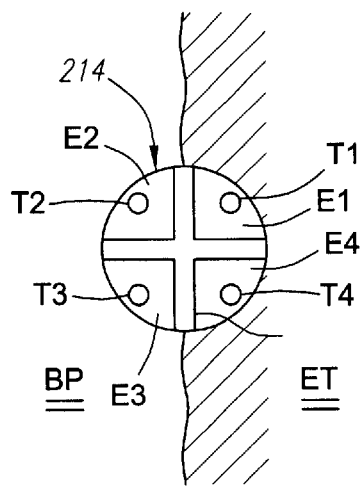
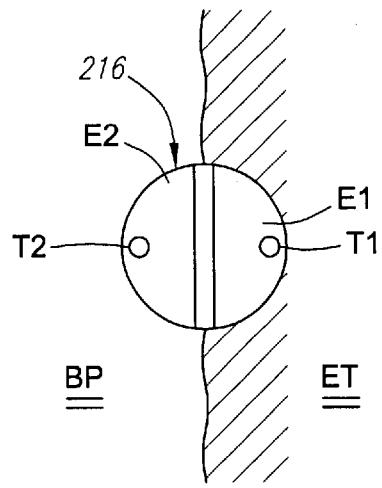
FIG. 17    FIG. 18

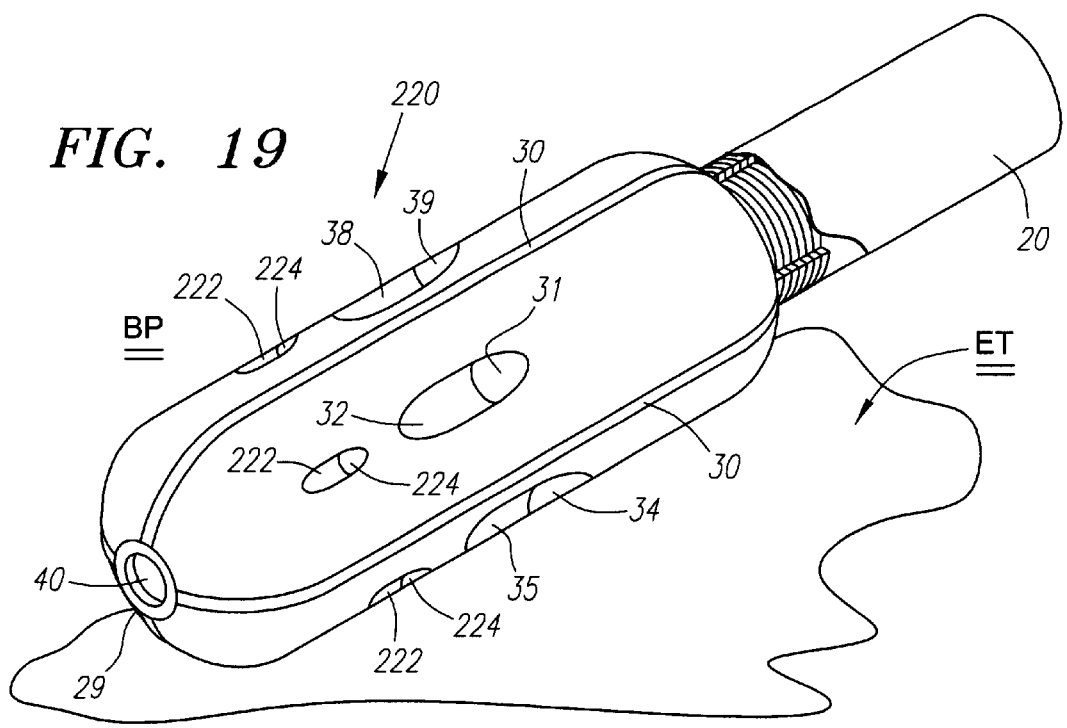
FIG. 19
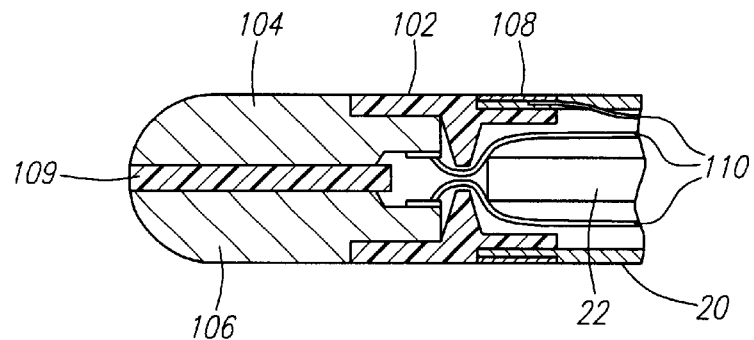
FIG. 20
FIG. 21

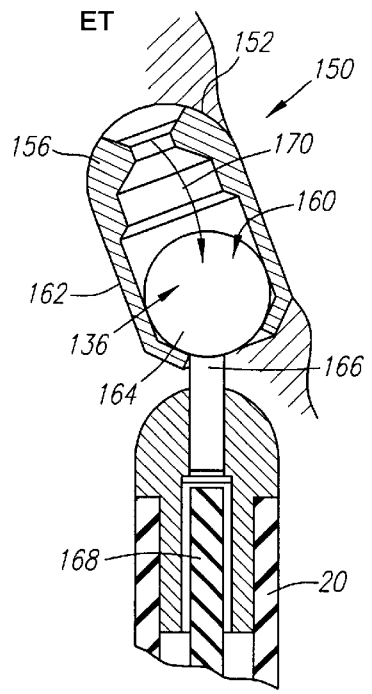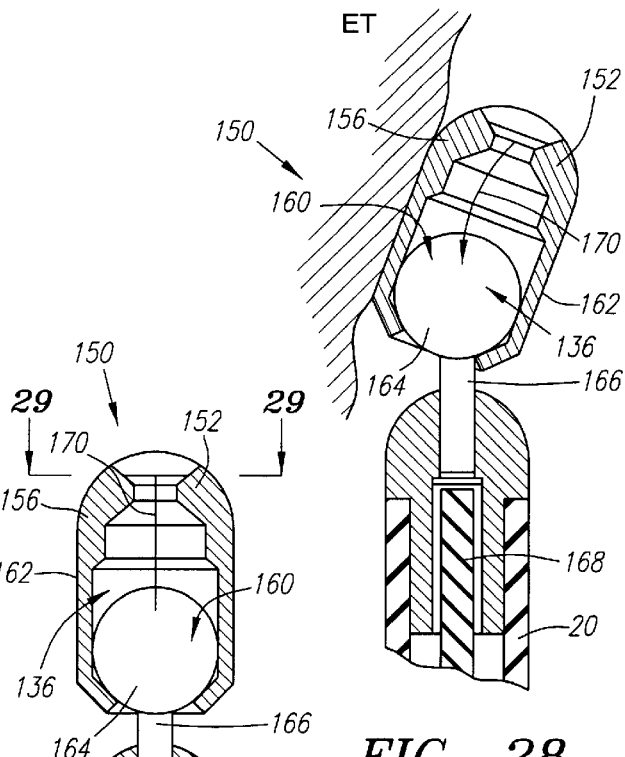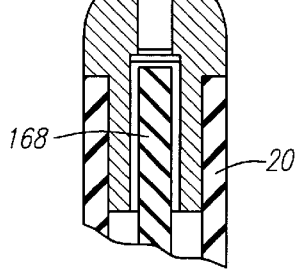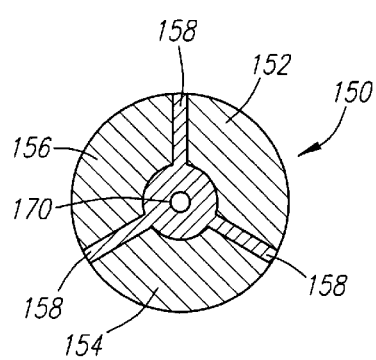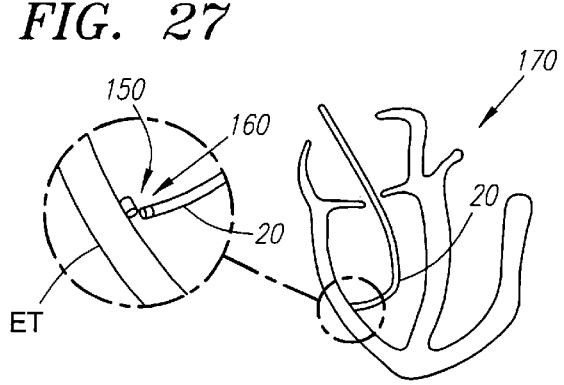

SYSTEMS AND METHODS FOR CREATING LESIONS IN BODY TISSUE USING SEGMENTED ELECTRODE ASSEMBLIES

This is a continuation of application Ser. No. 08/139,304 filed on Oct. 19, 1993, now abandoned.

FIELD OF THE INVENTION

In a general sense, the invention is directed to systems and methods for creating lesions in the interior regions of the human body. In a more particular sense, the invention is directed to systems and methods for ablating heart tissue for treating cardiac conditions.

BACKGROUND OF THE INVENTION

Physicians frequently make use of catheters today in medical procedures to gain access into interior regions of the body. In some procedures, the catheter carries an energy emitting element on its distal tip to ablate body tissues.

In such procedures, the physician must establish stable and uniform contact between the energy emitting element and the tissue to be ablated. Upon establishing contact, the physician must then carefully apply ablating energy to the element for transmission to the tissue.

The need for precise control over the emission of ablating energy is especially critical during catheter-based procedures for ablating heart tissue. These procedures, called electrophysiology therapy, are becoming increasingly more widespread for treating cardiac rhythm disturbances, called arrhythmias.

Today, cardiac ablation procedures typically use radiofrequency (RF) energy to form a lesion in heart tissue.

Conventional cardiac ablation systems designed to cure re-entrant supra ventricular tachycardia (SVT), often create lesions in myocardial tissue with a penetration depth of about 3 to 5 mm and a lesion volume of less than 0.2 cm$^3$, depending upon the size of the electrode and the amount of power that is applied.

However, to consistently cure MVT by ablation, a penetration depth greater than 3 to 5 mm and a lesion volume of at least 1 cm$^3$ is estimated to be required.

The solution may lie in larger electrodes and higher power systems. Yet, implementing this solution may itself pose additional problems.

The amount of RF energy that must be conveyed to conventional electrodes to create even small therapeutic lesions is already quite high (upwards to 50 watts or more). This is because conventional RF emitting electrodes are very inefficient. Only about 25% of the RF energy delivered to the electrode is actually directed into the heart tissue. The rest of the RF energy is dissipated into the circulating blood pool within the heart.

As a result, finding a predictable relationship between required RF power input and lesion volumes is often problematic. Not only are the power output to input efficiencies quite low, but they are also highly variable among patients.

Furthermore, the delivery of even larger amounts of RF energy to conventional electrodes means the dissipation of even larger amounts of energy into the blood pool. The effects of local blood heating, like the creation of thrombotic emboli, become more pronounced.

There is a need for energy emitting electrodes that more uniformly direct larger amounts of energy into the tissue, and not into the surrounding blood pool.

There is also a need for energy emitting electrodes that require less input power to create therapeutic lesions, regardless of their size.

SUMMARY OF THE INVENTION

The invention provides systems and methods that simplify the creation of lesions in body tissue, such as in the heart.

One aspect of the invention provides a multiple electrode array for ablating tissue in a body. The array comprises a support body having an axis. The body carries at least two electrode segments that are circumferentially spaced from each other about the body axis. Insulation on the support body electrically and thermally isolates the separated electrode segments from each other. Signal wires attached to the separated electrode segments convey ablating energy independently to the separated electrode segments.

Because of its segmented structure, the array may be placed with a single electrode segment in contact with tissue. Alternatively, two or more segments may contact the tissue at one time. Because each segment is electrically isolated, and because each segment is independently served by its own signal wire, a physician can operate an ablation energy generator to selectively channel the ablation energy only to the segments actually contacting the tissue.

A segmented electrode element provides significant improvements in lesion generation effectiveness and efficiency.

Another aspect of the invention provides a segmented electrode array that includes an orientation sensing mechanism on the support body for sensing the orientation of the separated electrode segments relative to tissue. The orientation sensing mechanism senses among the electrode segments which electrode segment is in contact with tissue and which electrode segment is not in contact with tissue.

Another aspect of the invention provides a system that integrates the segmented electrode array, an orientation sensing mechanism, and an ablating energy source. In this arrangement, the ablating energy source conveys ablating energy only to the electrode segment or segments sensed as being in contact with tissue.

Another aspect of the invention provides a method of ablating tissue in a body. The method comprises the steps of introducing a multiple electrode array comprising at least two separated and electrically isolated electrode segments. The method senses the orientation of the separated electrode segments relative to tissue and generates an orientation signal that identifies which one of the electrode segments contacts tissue and which one of the electrode segments does not. The method conveys ablating energy only to the electrode segment or segments identified as contacting tissue and not to the electrode segment or segments identified as not contacting tissue.

BRIEF DESCRIPTION OF THE DRAWINGS

FIG. 8 is a side view, partially in section, of an alternate form of an electrode assembly that embodies the features of the invention;

FIG. 9 is an end view of the electrode assembly shown in FIG. 8;

FIG. 10 is a top view of the electrode assembly shown in FIG. 8;

FIG. 11 is a side view of an alternate form of an electrode assembly that embodies the features of the invention;

FIG. 12 is an end view of the electrode assembly of FIG. 11;

FIG. 13 is a side view of an alternate form of an electrode assembly that embodies the features of the invention;

FIG. 14 is an end view of the electrode assembly of FIG. 13;

FIG. 15 is a diagrammatic view of a prior art electrode in contact with heart tissue;

FIGS. 16 and 17 are diagrammatic views of an electrode assembly like that shown in FIGS. 2 to 6 when in contact in different orientations with heart tissue;

FIG. 18 is a diagrammatic view of an electrode assembly like that shown in FIGS. 8 to 10 when in contact with heart tissue;

FIG. 19 is a perspective view of an alternate form of an electrode assembly that embodies the features of the invention, shown in contact with endocardial tissue;

FIG. 20 is a side view of an alternate form of an electrode assembly that embodies the features of the invention;

FIG. 21 is a side section view of the electrode assembly shown in FIG. 20;

FIG. 26 is a side section view of another alternate form of an electrode assembly that embodies the features of the invention and that incorporates touch actuated orientation sensing, showing the assembly flexed in one direction in contact with heart tissue;

FIG. 27 is side section view of the assembly shown in FIG. 26, showing the assembly when not flexed in contact with heart tissue;

FIG. 28 is a side section view of the assembly shown in FIGS. 26 and 27, showing the assembly flexed in another direction in contact with heart tissue;

FIG. 29 is an end section view of the electrode assembly taken generally along line 29—29 in FIG. 27; and FIG. 30 is a diagrammatic view of the electrode assembly shown in FIGS. 26 to 28 flexed in contact with endocardial tissue within the heart.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The invention provides systems and methods for ablating tissue inside a living body.

The invention lends itself to use in many relatively non-invasive catheter-based procedures. In contrast with complex, invasive surgical procedures, these catheter-based procedures introduce ablation elements into interior regions of the body by steering them through a vein or artery.

The specification that follows focuses upon a particular field of use, which is the treatment of cardiac disease. Still, the diverse applicability of the invention in other fields of use will also become apparent.

Figure 1:
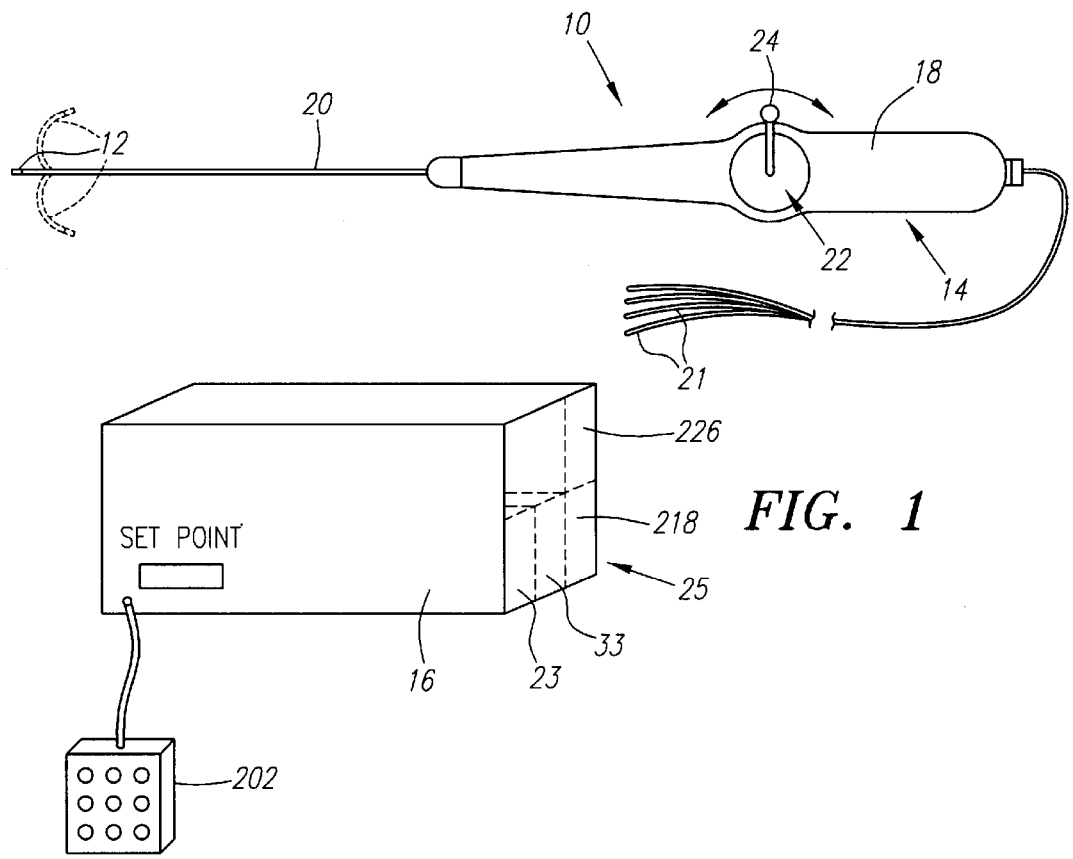
FIG. 1 is a perspective view of a cardiac ablation system that embodies the features of the invention.

FIG. 1 shows a cardiac ablation system 10 that embodies the features of the invention.

The system includes an electrode assembly 12 carried by a catheter 14. The system 10 also includes a controller 16.

The catheter 14 includes a handle 18 and a guide body 20. The distal end of the guide body 20 carries the electrode assembly 12.

The guide body 20 is made of an inert, flexible plastic material. Its proximal end is attached to the handle 18.

The catheter 18 includes a conventional catheter steering assembly 22. The steering assembly 22 serves to deflect the distal tip of the guide body 20, and, with it, the electrode assembly 12 itself (as shown in phantom lines in FIG. 1). The assembly 22 includes a control lever 24 to remotely to steer the electrode assembly 12.

FIGS. 2 to 6 show a preferred embodiment of the electrode assembly 12. According to one aspect of the invention, the electrode assembly 12 is segmented into multiple electrode element 26/27/28/29.

The electrodes elements 26/27/28/29 can be made of a solid, electrically conducting material, like platinum or gold, attached to the distal end of the catheter guide body 20. Alternatively, the electrode elements 26/27/28/29 can be formed by coating the exterior surface of an underlying support body (not shown) with an electrically conducting material, like platinum or gold. The coating can be applied using sputtering, ion beam deposition, or equivalent techniques.

The electrode elements 26/27/28/29 are electrically and thermally isolated one from the other by intermediate non-conducting zones 30. The zones 30 may, for example, comprise polystyrene or polycarbonate material.

Each electrode element 26/27/28/29 is electrically coupled to a signal wire 19 (see FIG. 2) made of an electrically conductive material, like copper alloy. The signal wires 19 extend through the guide body 20 into the handle 18.

One or more connectors 21 attach the proximal ends of the signal wires 19 (see FIG. 1) to the controller 16. The controller includes a module 23 for generating RF ablation energy. The generator 23 operates to apply ablating energy individually to a selected one or more of the electrode elements 26/27/28/29.

In use, the physician advances the catheter guide body 20 through an access vein or artery into the desired location in the heart. The physician observes the progress of the electrode element 12 using fluoroscopic or ultrasound imaging, or the like. The physician can manipulate the lever 22 to steer the element 12 into intimate contact with the desired region of heart tissue.

Figure 6:
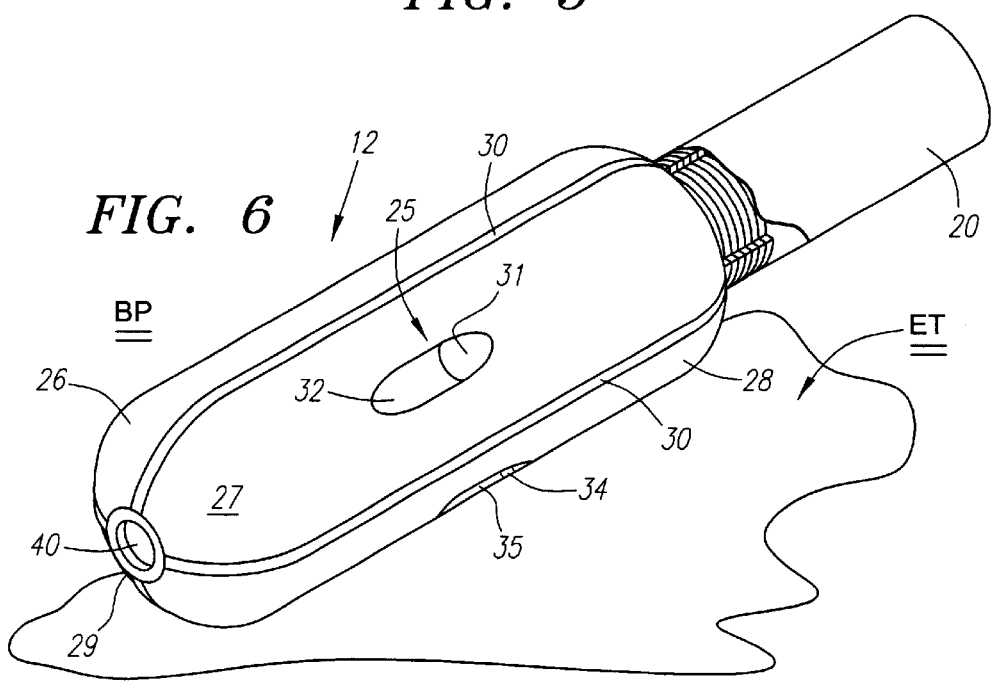
FIG. 6 is a perspective view, partially in section and broken away, of the electrode assembly shown in FIGS. 2 to 5 in contact with endocardial tissue.

As FIG. 6 shows, because of its segmented structure, the element 12 places one, and possibly two, of the electrode elements 26/27/28/29 in contact with endocardial tissue (designated ET in FIG. 6) at one time. Furthermore, because each element 26/27/28/29 is electrically and thermally isolated, and because each element 26/27/28/29 is independently served by its own signal wire 19, the physician can operate the RF generator 23 to selectively channel the ablation energy only to those elements actually contacting the tissue (which are elements 28 and 29 in FIG. 6.

As a result, the dissipation of energy into the blood pool (designated BP in FIG. 6) can be minimized. RF energy can be channelled directly into the heart tissue for ablation purposes.

According to another aspect of the invention, the controller 16 includes means 25 (see FIGS. 2 and 6) for identifying the particular electrode element or elements that are in contact with tissue. The identification means 25 interacts with the generator 23 to control the application of RF energy to the electrode assembly 10 based upon this input.

The identification means 25 can vary. In one preferred embodiment (see FIGS. 2 to 6), the identification means 25 includes a monitor module 33 (see FIG. 1) that senses temperature conditions in the environment immediately surrounding the electrode assembly 12. Based upon the temperature conditions sensed, the temperature monitor module 33 controls the generator 23 to specifically direct the application of RF energy to the electrode assembly 12.

In this arrangement (as FIGS. 2 to 6 show), the electrode elements 26/27/28/29 each includes an opening 32, 34, 36 and 38, respectively. The openings 32, 34, 36, and 38 carry temperature sensing devices 31, 35, 37 and 39, respectively.

The distal tip of the assembly 12 also carries an additional temperature sensing device 40. The temperature sensing device 40 may be contained in a non-conductive tubing, for example a thermoplastic polyester tubing.

The temperature sensing devices 31, 35, 37, 39, and 40 may be variously constructed. For example, they may take the form of conventional thermocouples, thermistors, or the like.

Figure 2:
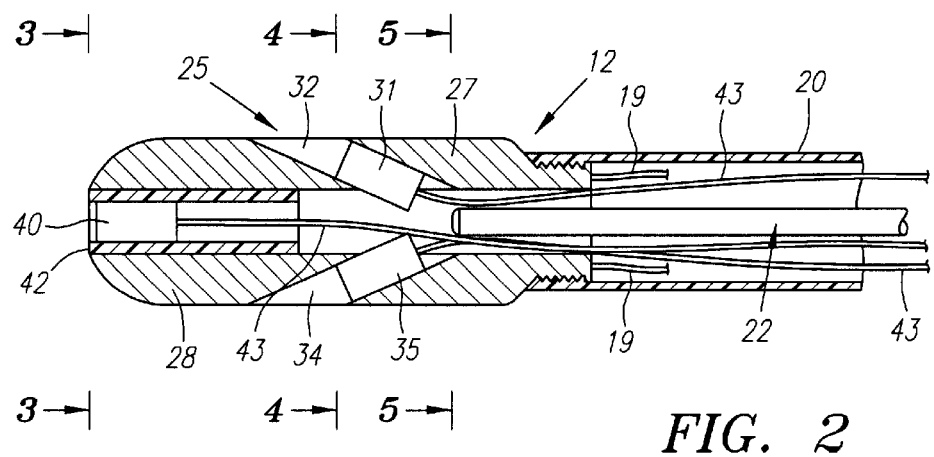
FIG. 2 is a central cross-sectional view of a segmented electrode assembly that the system shown in FIG. 1 incorporates.
Figure 3:
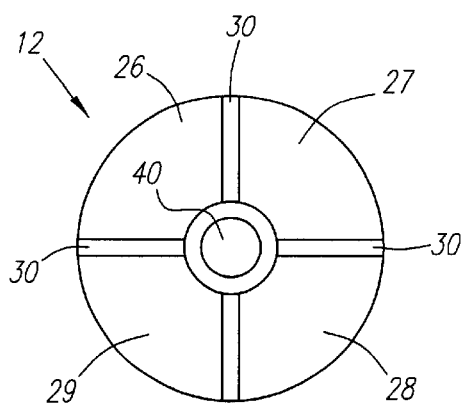
FIG. 3 is a cross-sectional view of the electrode assembly taken along line 3—3 of FIG. 2.
Figure 4:
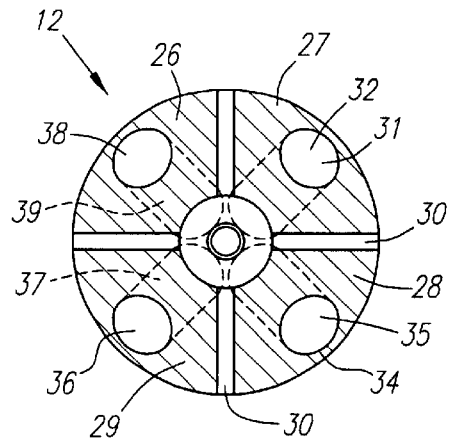
FIG. 4 is a cross-sectional view of the electrode assembly taken along line 4—4 of FIG. 2.
Figure 5:
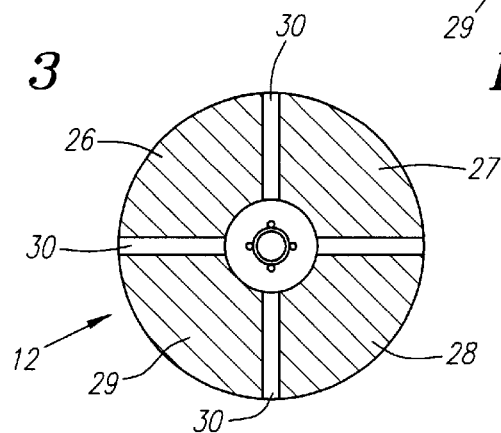
FIG. 5 is a cross-sectional view of the electrode assembly taken along line 5—5 of FIG. 2.

As best seen in FIG. 2, the devices 31, 35, 37, 39, and 40 are electrically coupled by signal wires 43 that extend through the guide body 20 to the temperature monitor module 33.

In use, the temperature sensing devices 31, 35, 37, 39, and 40 sense the temperatures of the environment in contact with various regions of the element 12. As FIG. 6 shows, depending upon the orientation of the element 12, the devices 31, 35, 37, 39, and 40 may sense the temperature of endocardial tissue ET, the blood pool BP, or a combination of both. Those sensing devices in contact, partially or entirely, with the blood pool BP will sense a lower temperature than the sensing devices in intimate contact with the tissue ET.

In the illustrated and preferred embodiment, the generator 23 is operated to initially apply RF energy to all electrode elements 22, 24, 26, and 28. The temperature monitor module 33 registers the temperatures sensed by the sensing devices 31, 35, 37, 39, and 40.

The temperature control module 33 includes a power control system 200 (see FIG. 7) for the generator 23. The control system 200 regulates the distribution and amount of RF energy delivered by the generator to the electrode assembly 12.

Figure 7:
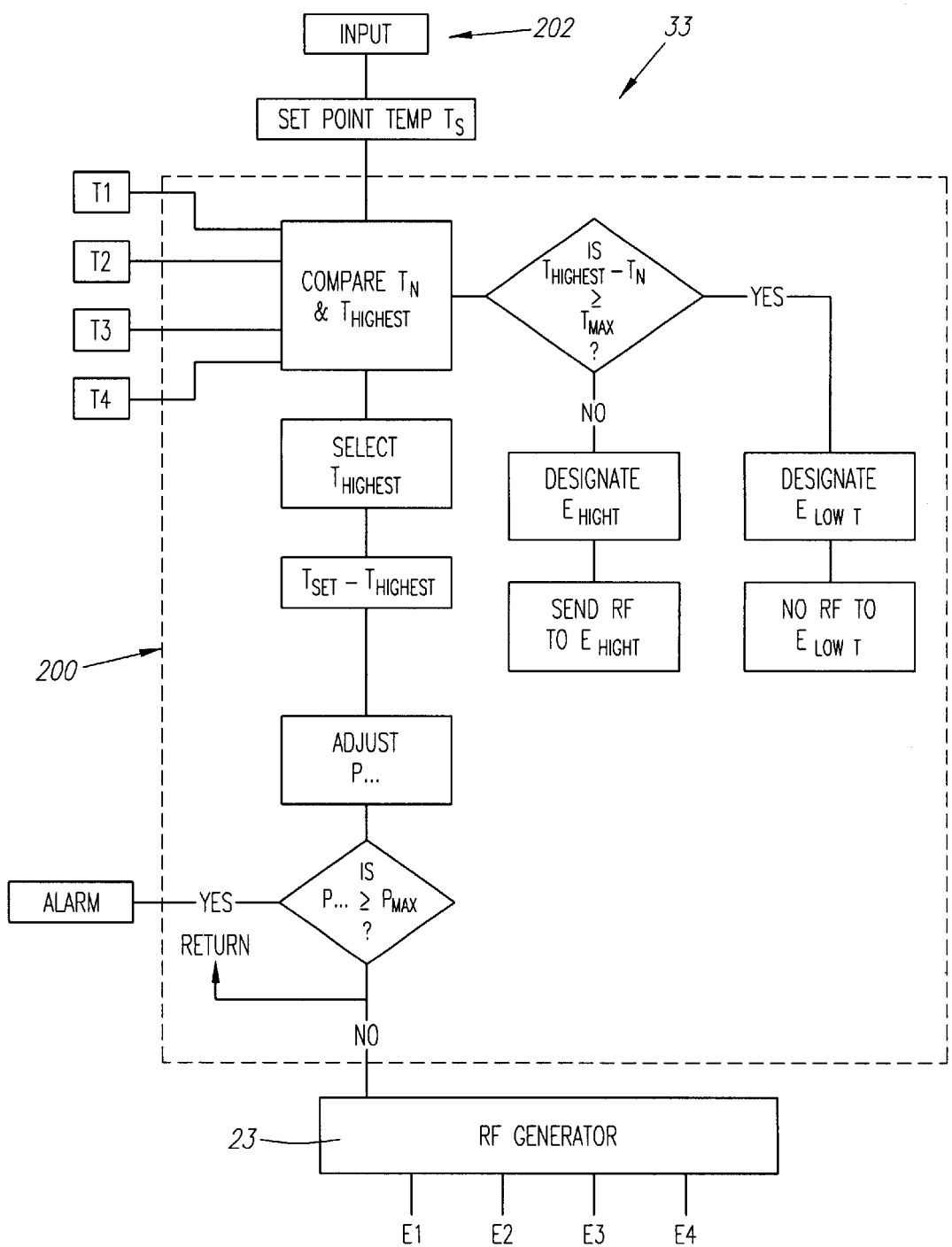
FIG. 7 is a diagrammatic flow chart showing the operation of the control system that uses temperature sensing to determine the orientation of the electrode assembly shown in FIG. 6 when in contact with heart tissue and to direct RF energy to it.

The control system 200 receives input from the temperature sensing devices, and determines all the sensed temperatures (designated T1, T2, T3, and T4 in FIG. 7). The control system 200 selects the greatest absolute sensed temperature ($T_{highest}$ in FIG. 7). The control system 200 compares the greatest sensed temperature $T_{highest}$ to the set point temperature (expressed as $T_{set}$ in FIG. 7). The deviation between $T_{highest}$ and $T_{set}$ becomes the control parameter for adjusting the power output P of the generator 23. The control system 200 adjust P to keep the greatest absolute sensed temperature $T_{highest}$ at or near the prescribed set point temperature $T_{set}$.

The control system 200 also preferably takes into consideration maximum power levels. If, responsive to command signals from the control system 200, power output P rises to a prescribed maximum power condition $P_{max}$, the control system 200 generates an alarm signal to alter the set power output, either by reducing it, shutting it off, or providing an alarm to the user, depending upon the control criteria selected.

The temperature monitor module 33 can also include an input device 202 (see FIGS. 1 and 7) for manually enter the desired maximum set point temperature $T_{set}$ sought during the ablation procedure.

The prescribed set point temperature condition $T_{set}$ can be set as high as 105 degrees C. The set point temperature condition anticipates where sensed electrical impedance of the tissue can be expected to rise sharply above the desired range of between 30 to 300 ohms. For human heart tissue, this rise in sensed tissue impedance typically occurs when tissue temperature enters the range of about 90 to 105 degrees C. and/or when blood coagulation occurs around the ablation electrode. The control system 200 also derives the deviation between each sensed temperature and the highest temperature condition (expressed as $T_{highest}-T_n$ in FIG. 7). The control system 200 compares a running average of each deviation ($T_{highest}-T_n$) to a prescribed maximum temperature difference (designated $T_{max}$ in FIG. 7). The preferred averaging period is about 0.1 to 2 seconds.

Those electrode elements whose sensed temperatures $T_n$ deviate from the highest temperature $T_{highest}$ by more than the prescribed amount $T_{max}$ are designated as the "coolest" electrode elements ($E_{low_t}$ in FIG. 7). These are the electrode elements that are in full or partial contact with the blood pool.

Those electrode elements whose sensed temperatures $T_n$ do not deviate from the highest temperature $T_{highest}$ by more than the prescribed amount $T_{max}$ are designated as the "hot" electrode elements ($E_{hight}$ in FIG. 7). These are the electrode elements that are in the most intimate contact with tissue.

As FIG. 7 shows, the control system 200 controls the generator 23 to interrupt the application of RF power to the identified "coolest" electrode elements $E_{low_t}$. The control system 200 directs the generator 23 to supply RF power only to the "hot" electrode element or elements $E_{hight}$.

The selected maximum deviation $T_{max}$ that differentiates between the "hot" (i.e., activated) electrode elements and the "coolest" (i.e., passive) electrode elements can vary, depending upon the sensitivity required. It is believed that a $T_{max}$ in the range of 5 to 15 degrees Centigrade is preferred.

Using the maximum sensed temperature condition $T_{highest}$ to control power output of the generator 23 assures patient safety, helps to prevent coagulation around the active electrode element or elements, and controls the parameters of the desired therapeutic results.

Of course, the number of segmented electrode elements on the element 10 can vary. For example, FIGS. 8 to 10 show an alternative segmented electrode assembly 10' having two electrode elements 52 and 54, which are electrically and thermally isolated by the electrical insulator 30. FIGS. 11 and 12 show another alternative segmented electrode assembly 10" having three electrode elements 62, 64, and 66, each of which are also electrically and thermally isolated from the other by the electrical insulator 30.

In both alternative embodiments, the electrode elements 52/54 and 62/64/66 are provided with openings (56/58 and FIGS. 8 to 10, and 63/65/67 in FIGS. 11 and 12) for carrying temperature sensing devices (not shown) for the purposes already described.

FIGS. 13 and 14 show yet another alternative arrangement for an electrode assembly 10''' that embodies features of the invention. In this embodiment, the electrode assembly 10''' includes electrode elements 72, 73, 74 and 75 separated by the electrically and thermally nonconductive material 30. Temperature sensing openings 76, 77, 78 and 79 are also provided to carry the temperature sensing devices. In this embodiment, the openings 76, 77, 78, and 79 are located between the electrode elements 72, 73, 74, and 75, rather than in the elements, as in the preceding embodiments.

It should therefore be appreciated that a diverse number of variations in the construction of segmented electrode elements 10 are possible.

The following Example demonstrates that a segmented electrode element (like that shown in FIGS. 1 to 14) provides significant improvements in lesion generation effectiveness and efficiency.

EXAMPLE

Ablations were performed in vitro on a lamb's heart in a saline bath held at a temperature of about 35 degrees Centigrade. A pump circulated saline across the heart surface to emulate blood flow conditions. Saline flowed at local velocities of 7, 11, and 16 cm/sec to simulate expected local flow rates at ablation sites within the heart.

The following control conditions were prescribed:
Maximum set point temperature: 80 degrees Centigrade.
Maximum RF power: 50 watts.
Period of ablation: 25 seconds.

FIG. 15 shows a prior art solid (i.e., unsegmented) platinum electrode 210 (measuring 8 French in diameter and 8 mm in length) with a central temperature sensing element T1, which was used as a control. The electrode 210 was operated under the above described control conditions. During the ablation period, the temperature sensor recorded a maximum sensed temperature of 86.04 degrees centigrade; a minimum sensed temperature of 52.29 degrees Centigrade; and an average sensed temperature of 78.02 degrees Centigrade. Under these control conditions, the generator applied to the electrode a minimum power of 25.47 watts; a maximum power of 49.07 watts; and an average power of 31.95 watts.

FIG. 16 shows a stainless steel electrode (also measuring 8 French in diameter and 8 mm in length) segmented into four elements E1, E2, E3, and E4, like electrode assembly 10 just described. Each element E1, E2, E3, and E4 carried its own temperature sensing element T1; T2; T3; and T4, respectively. During the ablation procedure, the electrode was oriented as shown in FIG. 16, with essentially only electrode element E1 in intimate contact with tissue ET. The other electrode E2, E3 and E4 were in full or substantial contact with the emulated blood pool BP.

RF energy was applied to electrode E1 only, with power controlled using feedback from T1 only.

The following Table 1 shows the range of temperatures sensed by T1; T2; T3; and T4 during the 25 second ablation period:

TABLE 1

|  | T1 | T2 | T3 | T4 |
| --- | --- | --- | --- | --- |
| Average | 78.58 | 38.59 | 46.27 | 48.08 |
| Maximum | 83.7 | 41.5 | 49.45 | 50.47 |
| Minimum | 64.99 | 35.71 | 42.69 | 41.19 |

\*\* In Degrees Centigrade

Only electrode E1 received RF energy during the 25 second ablation period. To maintain the T1 temperatures set forth in Table 1, the generator applied to the electrode E1 a minimum power of 2.39 watts; a maximum power of 13.92 watts; and an average power of 5.62 watts.

The control electrode 210 (FIG. 15) and the segmented electrode 212 (FIG. 16) formed comparable lesions, yet the segmented electrode 210 required on the average only ⅙th the RF power the control electrode 210 required under the same control conditions.

FIG. 17 shows another stainless steel electrode 214 (also measuring 8 French in diameter and 8 mm in length) segmented into four elements E1, E2, E3, and E4, like electrode assembly 10 just described. Each element E1, E2, E3, and E4 carried its own temperature sensing element T1; T2; T3; and T4, respectively. During the ablation procedure, the electrode was oriented as shown in FIG. 17, with both electrode elements E1 and E4 in intimate contact with tissue ET. The other electrodes E2 and E3 were in full contact with the emulated blood pool BP.

RF energy was applied to electrodes E1 and E@ only, with power controlled using feedback from T1 only.

The following Table 2 shows the range of temperatures sensed by T1; T2; T3; and T4 during the 25 second ablation period:

TABLE 2

|  | T1 | T2 | T3 | T4 |
| --- | --- | --- | --- | --- |
| Average | 79.37 | 37.55 | 42.67 | 85.94 |
| Maximum | 84.86 | 39.34 | 46.18 | 93.21 |
| Minimum | 73.11 | 35.29 | 39.83 | 79.73 |

\*\* In Degrees Centigrade

Electrodes E1 and E4 each received RF energy during the 25 second ablation period. To maintain the T1 temperature set forth in Table 2, the generator applied to electrodes E1 and E4 a minimum power of 0.73 watts; a maximum power of 15.38 watts; and an average power of 8.8 watts.

Again, the control electrode 210 (FIG. 15) and the segmented electrode 214 (FIG. 17) formed comparable lesions, yet the segmented electrode 214 required on the average only ⅓rd the RF power the control electrode 210 required under the same control conditions.

FIG. 18 shows another stainless steel electrode 216 (also measuring 8 French in diameter and 8 mm in length) segmented into two elements E1 and E2, like that shown in FIGS. 8 to 10. Each element E1 and E2 carried its own temperature sensing element T1 and T2, respectively. During the ablation procedure, the electrode was oriented as shown in FIG. 18, with only electrode element E1 in intimate contact with tissue ET. The other electrode E2 was in full contact with the emulated blood pool BP.

The following Table 3 shows the range of temperatures sensed by T1 and T2 during the 25 second ablation period:

TABLE 3

|  | T1 | T2 |
|---|---|---|
| Average | 79.9 | 40.95 |
| Maximum | 82.55 | 44.5 |
| Minimum | 72.56 | 38.52 |

** In Degrees Centigrade

Electrode E1 received RF energy during the 25 second ablation period. To maintain the T1 temperatures set forth in Table 3, the generator applied to electrode E1 a minimum power of 0.73 watts; a maximum power of 16.85 watts; and an average power of 12.68 watts.

Again, the control electrode 210 (FIG. 15) and the segmented electrode 216 (FIG. 18) formed comparable lesions, yet the segmented electrode 210 required on the average less than ½ the RF power the control electrode 210 required under the same control conditions.

The segmented electrode design has a further benefit in addition to that of improved ablation efficiency. The "hottest" electrode segment is very close to the highest temperature in the tissue. When the radiofrequency energy is applied to one or more active electrode segments, applied power density is highest next to those segments. Since the "hottest" electrode segment is thermally isolated from cooler electrode segments, heat is constrained to flow into the tissue, with the highest temperatures maintained at the electrode-tissue interface. Since the electrode segment is in intimate contact with the tissue, and since the thermal capacity of the electrode is small compared to that of tissue, the electrode segment rapidly comes to thermal equilibrium with the tissue surface. Therefore, for the segmented tip design, the control system 200 maintains the hottest tissue temperature near $T_{set}$, which is the preferred method for temperature feedback control.

In contrast, a solid metal ablation tip always has a portion of its surface exposed to blood, which cools it. If the blood is flowing past the tip, that cooling rate is even higher. Since the metal tip is in intimate thermal contact with the tissue, the surface tissue is also cooled significantly. Therefore, the heat produced by the radiofrequency current can flow both into the tissue and through the tip into the blood pool. In this case, the hottest tissue temperature is within the bulk of the tissue, rather than at the interface of the tissue and electrode tip. The inventors have experimentally determined that, for conventional tips, the hottest tissue temperature is 1 to 2 mm from the ablation electrode tip when using 500 kHz radiofrequency current to ablate the tissue. With a solid ablation tip, the control system 200 allows the hottest tissue temperature to considerably exceed $T_{set}$, which is not ideal.

The identification means 25 can sense the orientation of a segmented electrode assembly 10 relative to tissue ET in alternative ways. For example, referring to the assembly 10 shown in FIGS. 1 to 6, the controller 16 includes a stimulation means (pacemaker) and a signal monitor module 218 that receives electrogram signals from the electrode elements 26/27/38/29. The electrogram signals reflect the electrical activity sensed by each element and can be used to determine if the pacemaker successfully captured the heart.

Only those electrode elements (as shown in FIG. 6, the elements 28 and 29) in contact with the tissue ET will successfully capture the heart using normal pacing amplitudes. The signal monitor module 218 controls the generator to convey RF energy only those identified electrode elements 28 and 29 to carry out the ablation procedure.

In another alternative arrangement (see FIG. 19), the electrode assembly 220 is similar in most respects to the electrode assembly 10 shown in FIGS. 1 to 6. It includes the same multiple electrode elements 26/27/28/29 separated by electrically and thermally nonconductive material 30. It also carries the same array of temperature sensing devices 31/35/37/39/40.

Unlike the assembly 10, the assembly 220 includes an additional opening 222 in each element 26/27/28/29. The additional openings 222 carry pressure transducers 224 that sense contact with tissue ET. In this arrangement, the pressure transducers 224, when sensing contact with tissue ET, convey signals to a pressure contact module 226 in the controller 16. The other pressure transducers 224 exposed to the blood pool BP will not sense contact and will therefore not convey signals. The module 226 identifies those electrode element or elements associated with the pressure transducer signals. The module 226 directs the generator to convey RF energy to these elements, and not to the elements in the blood pool BP.

Either of these alternative embodiments can operate in tandem with the control system 200 based upon temperature sensing, described above. Once the signal monitor 218 or pressure sensing module 226 identify the electrode element or elements in contact with tissue, the described temperature control system 200 can thereafter adjust the set power output $P_{set}$ of the generator 23 to the selected electrode element or elements based upon $T_{highest}$ to keep the temperature sensed by the associated sensor at or near the prescribed set point temperature $T_{set}$, keeping in mind the predetermined operative maximum power level $P_{max}$.

FIGS. 20 and 21 show another alternative arrangement for identifying the position of a segmented electrode assembly relative to heart tissue. In this embodiment, the electrode assembly 100 includes electrode elements 104 and 106 having different lengths. This arrangement allows the use of an external fluoroscope monitor (not shown) to identify the relative positions of the electrode elements.

More particularly, in the embodiment shown in FIGS. 20 and 21, due to their difference in size, each element 104 and 106 will project a different fluoroscopic image. The different fluoroscopic images makes it possible for the physician to remotely differentiate the two elements 104 and 106 to discern which electrode element 104 or 106 is in contact with the tissue.

Figure 22:
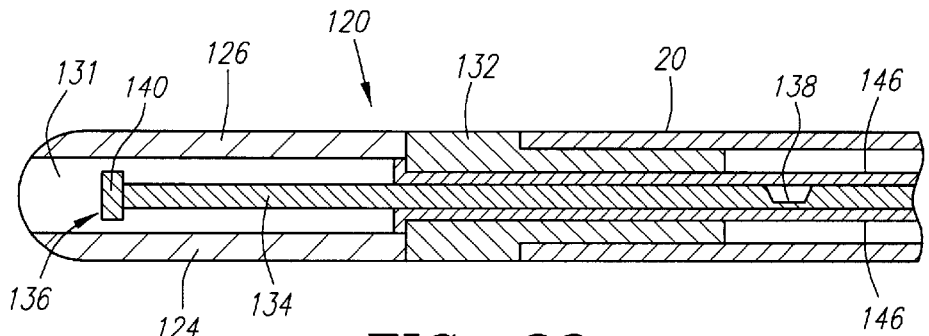
FIG. 22 is a side section view of another alternate form of an electrode assembly that embodies the features of the invention and that incorporates touch actuated orientation sensing.
Figure 23:
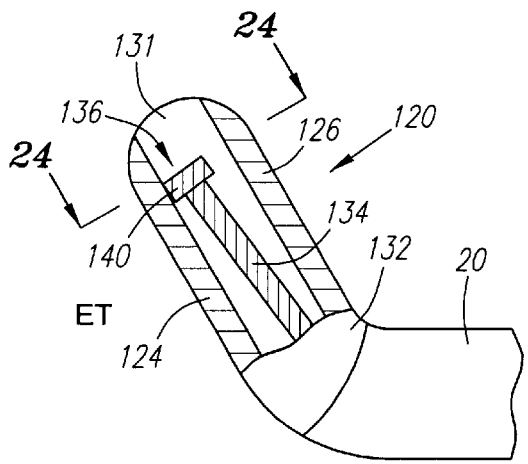
FIG. 23 is a side view, partially in section and broken away, of the electrode assembly shown in FIG. 22, with the assembly flexed in contact with endocardial tissue.
Figure 24:
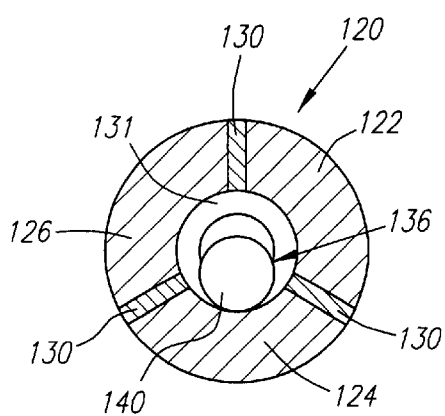
FIG. 24 is a section view taken along line 24—24 in FIG. 23.

FIGS. 22 to 24 show a segmented electrode assembly 120 with contact activated orientation sensing capabilities.

The assembly 120 includes three electrode elements 122, 124 and 126. As in previous embodiments, the elements 122, 124, and 126 are separated by electrically and thermally non-conductive material 130 (see FIG. 24).

As shown in FIG. 22, the elements 122/124/126 and the intermediate material 130 collectively encircle a hollow interior space 131 within the assembly 120.

According to this aspect of the invention, the assembly 120 includes means 136 for sensing which electrode element 122, 124, and 126 is in contact with tissue in response to pressure or touch contact between the assembly 120 and tissue.

The pressure activation means 136 includes a plug 132 of non-conductive material (see FIG. 22) that joins the assembly 120 to the distal end of the associated catheter guide body 20. The material for the plug 132 can be a polyurethane polymer or the like.

As FIG. 23 shows, the electrode assembly 120 bends or flexes about the plug 132 when urged into contact with tissue ET within the heart.

The activation means 136 further includes a relatively stiff cable member 134 that passes through an bore in the plug 132 into the hollow interior space 131 of the assembly 120.

The cable member 134 includes a contact 140 on its distal end, which extends within the interior space 131. As FIG. 23 shows, flexing of the assembly 120 about the plug 132 brings the interior surface of one or more of the electrode elements 122/124/126 into electrical contact with the contact tip 140.

Which electrode element(s) contacts the tip 140 depends upon which direction the flexing occurs. According to this aspect of the invention, however, when the assembly 120 is urged into contact with tissue ET (as FIG. 23 shows), the flexing causes electrical contact to be made between the tip 140 and the electrode element that is in the most intimate touch contact with the tissue (which, in FIG. 23, is electrode element 124).

Figure 25:
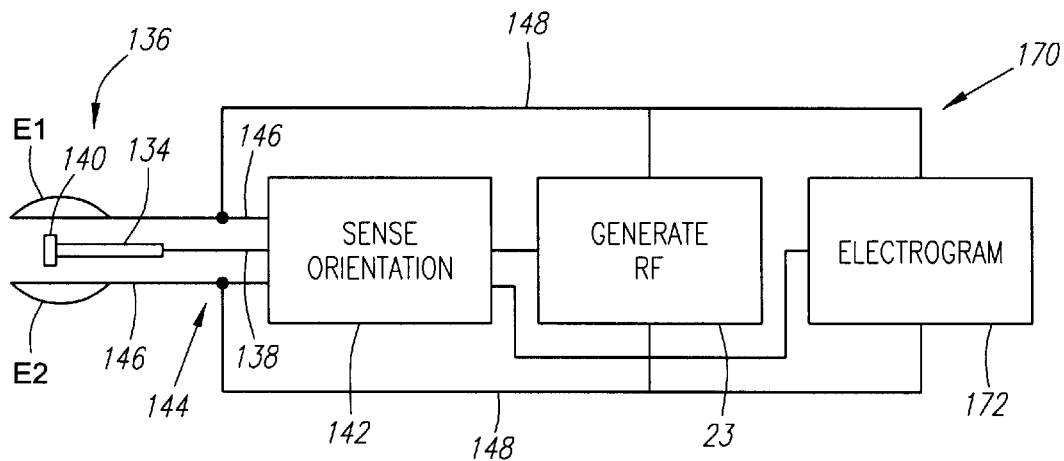
FIG. 25 is a diagrammatic view of the orientation sensing circuit associated with the electrode assembly shown in FIGS. 23 and 24.

The cable member 134 includes a core conductor 138 (see FIG. 22) that is electrically coupled to the tip 140 (see FIGS. 22 and 25). The core conductor 138 extends back through the guide body 20 and associated handle 18 to make electrical connection with an orientation sensing module 142 (see FIG. 23). The core conductor 138 forms a part of an orientation sensing circuit 144 for the electrode elements.

As FIGS. 22 and 25 show, the sensing circuit 144 includes signal wires 146 electrically coupled to each electrode element (symbolically designated E1 and E2 in FIG. 25). The signal wires 146 are also electrically coupled to the orientation sensing module 142. The signal wires represent the electrical return path, while the core conductor 138 represents the electrical supply path of the circuit 144 coupled to the orientation sensing module 142.

The tip 140 and the electrode element E1/E2 act as switches in the circuit 144. When out of contact with the electrode elements E1/E2 the sensing circuit 144 is electrically open.

When the tip 140 contacts the electrode element E1 or E2 that is in contact with tissue, the contact closes the sensing circuit 144 through that electrode element E1 or E2.

The orientation sensing module 142 identifies the electrode element E1 or E2 that has closed the circuit 144. The module 142 directs the generator 23 to convey RF energy to it.

In the illustrated and preferred embodiment, signal wires 148 convey RF energy from the generator 23. The signal wires 148 are electrically coupled to the signal wires 146 to carry the RF energy to the selected electrode element (see FIGS. 22 and 25). The signal wires 146 and 148 are of a higher gauge and can carry more power than the core conductor 138 of the orientation sensing circuit 144. As FIG. 25 shows, the signal wires 146 and 148 also form a circuit 170 that can carry electrical potential signals sensed in heart tissue by the selected electrode element to an electrogram device 172.

Thus, the means 136 identifies the electrode element that is in contact with tissue, so that RF energy can be transmitted directly to it for ablation purposes, or so that electrical potential signals sensed in the tissue contacted by the electrode can be transmitted directly from it for electrogram analysis.

A further embodiment of this invention has a means for determining the force of the catheter tip against the cardiac tissue. Narrow strips of thin Piezo electric film (not shown) are placed on the interior surfaces of electrode elements 122/124/126 so as to be contacted by tip 140 when the electrode assembly bends or flexes about the plug 132 when urged into contact with tissue ET within the heart. Insulated wires that are retained within the catheter body would be attached at one end to the inside of the film (one electrode to each side) and at the other end to the connector in the handle. The voltage produced across the film is proportional to the force that tip 140 exerts against the film. Thus, by using the voltage generated across the film, an assessment could be made as the position stability of the electrode assembly on the tissue ET. The voltage could be displayed for use by the operator, or it could be used by a controller to determine which of the electrode elements 122/124/126 to activate.

Other small dimensional pressure transducers could be used in place of the piezo electric film to determine tip pressure on the electrode elements without affecting device function. Also, for this embodiment of the invention, the tip 140 need not directly contact the inside surface of the electrode elements. For example, tip 140 could contact pressure sensitive film on the inside of the distal tubing proximal to the electrode assembly 120. Since contact pressure is used to determine the location of the electrode elements 122/124/126 relative to the tissue ET, no direct electrical contact with the electrode elements is required.

FIGS. 26 to 29 show another embodiment of a segmented electrode assembly 150 with contact activated orientation sensing capabilities.

The assembly 150 includes multiple electrode elements, which, in the illustrated embodiment, number three 152, 154, and 156 (see FIG. 29). As in previous embodiments, the elements 152/154/156 are separated by electrically and thermally non-conductive material 158 (see FIG. 29).

The sensing means 136 in FIGS. 26 to 29 includes an articulated joint 160 that joins the assembly 150 to the distal end of the associated catheter guide body 20. The joint 160 comprises a socket element 162 and a ball element 164.

The socket element 162 is carried within the interior of the assembly 150. It is made from an electrically and thermally nonconducting material, like polycarbonate.

The ball element 164 is formed from a conductive material that nests within the socket. The ball is attached to an electrically conducting stem 166. The stem 166, in turn, is electrically coupled by a signal wire 168 to the RF generator.

As FIGS. 26 and 28 show, the electrode assembly 150 flexes about the ball and socket joint 160 when urged into contact with tissue ET.

The sensing means 136 in this embodiment further includes a flexible leaf switch element 170 carried at the distal end of the ball element 164. Flexing of the assembly 150 about the ball and socket joint 160 brings the interior surface of one of the electrode elements 152/154/156 into electrical contact with the leaf switch element 170.

Which electrode element contacts the leaf switch element 170 depends upon which direction the flexing occurs. However, as FIGS. 26 and 28 show, when the assembly 150 is urged into contact with tissue ET, the flexing causes electrical contact to be made between the leaf switch element 170 and the electrode element that is in touch contact with the tissue. In FIG. 26, electrode element 152 is in contact both with the tissue ET and the switch element 170. In FIG. 28, electrode element 156 is in contact both with the tissue ET and the switch element 170. FIG. 30 further shows the flexing of the assembly 150 urged against tissue ET within the heart 170.

In this embodiment, the RF generator circuit and the orientation sensing circuit are one and the same. The signal wire 168, the ball element 164, and the leaf switch element 170 directly conduct RF energy from the generator to the electrode element which the leaf switch element 170 contacts. Still, the assembly 150 can be used in association with a separate orientation sensing circuit in the manner shown in FIG. 25.

Therefore, when urged into contact with tissue ET, the leaf switch element 170 makes electrical contact with the electrode element that is in contact with the tissue. The leaf switch element 170 closes the circuit to convey RF energy to the element.

As in the embodiment shown in FIGS. 22 to 24, the touch sensitive means 136 identifies the electrode element that is in contact with tissue for application of RF energy.

By providing the alternative electrode assemblies 120 and 150 with temperature sensing devices as shown in the FIGS. 2 to 6, the touch activation means 136 can operate in tandem with the temperature sensing control system 200. Once the activation means 136 switches on the appropriate electrode element, the described temperature control system 200 can thereafter alter the output voltage of the generator to the selected electrode element to keep the temperature sensed by the associated sensor at or near the prescribed set point temperature, keeping in mind the predetermined operative maximum and minimum power levels.

Various further features and benefits of the inventions are set forth in the following claims.

We claim:

1. A system for ablating tissue in a body, comprising:
   a guide body having a distal end,
   a multiple electrode array carried on the distal end of the guide body comprising
   a support body having an axis,
   at least first and second electrodes on the support body, the electrodes being circumferentially spaced from each other about the body axis, said body being adapted to be oriented generally parallel to the surface of said tissue when at least one of said electrodes is in contact with said tissue and at least one of said electrodes is in contact with a blood pool adjacent to said tissue,
   an insulator on the support body for electrically isolating the separated electrodes from each other,
   first and second wires attached to the separated electrodes for conveying ablating energy independently to the separated electrodes, and
   a controller electrically coupled to the first and second wires for conveying ablating energy to the one of the electrodes which is in contact with the tissue while not conveying energy to the other of the electrodes which is in contact with said blood pool.

2. A system according to claim 1
   wherein the separated and electrically isolated electrodes comprise at least three circumferentially spaced electrodes.

3. A system according to claim 1
   wherein the separated and electrically isolated electrodes comprise at least four circumferentially spaced electrodes.

4. A system according to claim 1,
   further including an orientation sensor on the support body the orientation sensor configured for sensing the orientation of the separated and electrically isolated electrodes relative to the tissue and for generating an orientation signal,
   wherein the controller conveys ablating energy at least in response to the orientation signal.

5. A system according to claim 4,
   wherein the orientation sensor includes a switch within the support body that contacts one of the electrodes when the one electrode contacts tissue while not contacting the remaining electrodes not in contact with tissue, and
   a sensor to determine contact between the switch and the one electrode, the sensor configured to generate the orientation signal which identifies among the electrodes the one electrode that contacts tissue.

6. A system according to claim 5,
   wherein the controller conveys ablating energy only to the one electrode identified as contacting tissue.

7. A system according to claim 4,
   wherein the orientation signal identifies among the electrodes which of the electrodes are contacting tissue and which of the electrodes are not contacting tissue, and
   wherein the controller conveys ablating energy to the electrodes identified as contacting tissue while not conveying ablating energy to the electrodes identified as not contacting tissue.

8. A system for ablating tissue in a body comprising:
   a guide body having a distal end,
   a support body, having an axis, carried on the distal end of the guide body,
   a first electrode on the support body, first electrode and electrically isolated from the first electrode,
   a first conductor coupled to the first electrode for conveying ablating energy to the first electrode,
   a second conductor coupled to the second electrode for conveying ablating energy to the second electrode independently of the first electrode,
   a first temperature sensor associated with the first electrode for sensing temperature conditions adjacent the first electrode,
   a second temperature sensor associated with the second electrode for sensing temperature conditions adjacent the second electrode,
   a comparator coupled to the first and second temperature sensors for comparing the temperature conditions adjacent the first and second electrodes and, based thereon, identifying which of the first and second electrodes is contacting tissue and which of the first and second electrodes is not contacting tissue, and
   a controller coupled to the comparator and to the first and second conductors for conveying ablating energy to whichever one of the first or second electrodes is contacting tissue as identified by the comparator.

9. A system according to claim 8
   wherein the controller does not convey ablating energy to whichever one of the first and second electrodes is not contacting tissue as identified by the comparator.

10. A system for ablating tissue in a body comprising:
    a guide body having a distal end, and
    a multiple electrode array carried on the distal end of the guide body, the multiple electrode array comprising:
    a support body having an axis,
    at least first and second electrodes on the support body, the electrodes being circumferentially spaced from each other about the body axis, the body being adapted to be oriented generally parallel to the surface of the tissue when the electrodes are placed in contact with the tissue, at least one of the electrodes contacting the tissue and at least one of the electrodes being in contact with a blood pool adjacent the tissue, an insulator on the support body for electrically isolating the electrodes from each other, and a plurality of conductors for conveying ablating energy independently to the electrodes, the system further comprising:

an orientation sensor on the support body for sensing the orientation of the electrodes relative to the tissue and generating an orientation signal indicative thereof, and a controller responsive to the orientation signal and electrically coupled to the conductors for conveying ablating energy to one of the electrodes which is in contact with the tissue while not conveying ablating energy to the other of the electrodes which is in contact with the blood pool, the orientation sensor including:

a pressure sensor associated with each of the electrodes for sensing contact pressure adjacent the associated electrode, and a comparator coupled to the pressure sensors for comparing the contact pressures sensed adjacent the electrodes and generating the orientation signal based on the comparison.

11. A system according to claim 10 wherein the controller conveys ablating energy only to whichever ones of the electrodes are contacting tissue as identified by the comparator.

12. A method of ablating tissue in a body, comprising the steps of:

introducing a multiple electrode array into the body, the multiple electrode array comprising at least first and second electrodes on a support body, the electrodes being circumferentially spaced from each other about the axis of the support body, sensing the orientation of the separated electrodes relative to the tissue and generating an orientation signal, and conveying ablating energy to one of the electrodes while not conveying ablating energy to another one of the electrodes in response at least in part to the orientation signal.

13. A method of ablating tissue in a body, comprising the steps of:

introducing a multiple electrode array into the body, the multiple electrode array comprising at least first and second electrodes on a support body, the electrodes being circumferentially spaced from each other about the axis of the support body, sensing the orientation of the separated electrodes relative to the tissue and generating an orientation signal that identifies which one of the electrodes contacts the tissue and which one of the electrodes does not contact the tissue, and conveying ablating energy only to the electrodes identified as contacting the tissue and not to the electrodes identified as not contacting the tissue.

* * * * *